(12) United States Patent
Landman et al.

(10) Patent No.: US 7,811,256 B2
(45) Date of Patent: Oct. 12, 2010

(54) VACUUM ASPIRATION HANDLE

(75) Inventors: Jaime Landman, New York, NY (US); John H. Ward, Spencer, IN (US); Walter N. Ryan, Greenville, NC (US); Mahfuza Ahmed, Bloomington, IN (US); Gregory A. Frankland, Bloomington, IN (US); Scott K. Philhower, Bloomington, IN (US)

(73) Assignees: Vance Products Inc., Spencer, IN (US); Sabin Corporation, Bloomington, IN (US)

( * ) Notice: Subject to any disclaimer, the term of this patent is extended or adjusted under 35 U.S.C. 154(b) by 0 days.

(21) Appl. No.: 12/338,590

(22) Filed: Dec. 18, 2008

(65) Prior Publication Data

US 2009/0187146 A1    Jul. 23, 2009

Related U.S. Application Data

(60) Provisional application No. 61/015,004, filed on Dec. 19, 2007.

(51) Int. Cl.
*A61M 1/00* (2006.01)
*A61M 37/00* (2006.01)

(52) U.S. Cl. ...................... 604/119; 604/131

(58) Field of Classification Search ............... 604/119, 604/25, 205, 128, 35, 118, 131; 433/29
See application file for complete search history.

(56) References Cited

U.S. PATENT DOCUMENTS

| 4,095,667 A | 6/1978 | Mahig et al. |
| 4,727,875 A | 3/1988 | Dory |
| 5,160,336 A | 11/1992 | Favre |
| 5,186,714 A | 2/1993 | Boudreault et al. |

(Continued)

FOREIGN PATENT DOCUMENTS

| FR | 455 868 | 6/1912 |

(Continued)

OTHER PUBLICATIONS

Search Report and Written Opinion dated Apr. 14, 2009 for related PCT/US2008/087330.

(Continued)

*Primary Examiner*—Nicholas D Lucchesi
*Assistant Examiner*—Rebecca E Eisenberg
(74) *Attorney, Agent, or Firm*—Brinks Hofer Gilson & Lione (57) ABSTRACT

A medical device is provided. The medical device includes a sheath with an extended distal end portion, a proximal end portion, and a lumen defined therethrough. A handle is fixedly connected to the proximal end portion of the sheath, the handle includes an operator that is translatable between a first position and a second position. A flow path is defined within the handle in fluid communication with the proximal end portion of the sheath, wherein the operator is configured to substantially block the flow path in a second position and allow flow therethrough in a first position. The flow path includes a portion that is configured to communicate with a remote source of suction. The handle additionally includes a second inlet portion configured to receive a tool therethrough and allow the tool to extend through the lumen of the sheath.

18 Claims, 8 Drawing Sheets

U.S. PATENT DOCUMENTS

| | | | |
|---|---|---|---|
| 5,265,840 A | | 11/1993 | Gillespie et al. |
| 5,273,524 A | * | 12/1993 | Fox et al. ............... 604/21 |
| 5,312,327 A | | 5/1994 | Bales et al. |
| 5,312,332 A | | 5/1994 | Bales et al. |
| 5,314,406 A | | 5/1994 | Arias et al. |
| 5,336,172 A | | 8/1994 | Bales et al. |
| 5,336,220 A | | 8/1994 | Ryan et al. |
| 5,350,356 A | | 9/1994 | Bales et al. |
| 5,354,291 A | | 10/1994 | Bales et al. |
| 5,409,013 A | * | 4/1995 | Clement ............... 600/566 |
| 5,429,596 A | | 7/1995 | Arias et al. |
| 5,549,547 A | | 8/1996 | Cohen et al. |
| 5,722,980 A | | 3/1998 | Schulz et al. |
| 5,735,849 A | * | 4/1998 | Baden et al. ............ 606/51 |
| 5,746,721 A | * | 5/1998 | Pasch et al. ............ 604/153 |
| 5,868,756 A | | 2/1999 | Henry et al. |
| 6,090,094 A | * | 7/2000 | Clifford et al. ............ 604/500 |
| 6,375,651 B2 | | 4/2002 | Grasso, III et al. |
| 6,511,485 B2 | | 1/2003 | Hirt et al. |
| 6,517,531 B2 | | 2/2003 | Liu et al. |
| 6,669,685 B1 | * | 12/2003 | Rizoiu et al. ............ 606/10 |
| 7,470,274 B2 | | 12/2008 | Lebet |
| 7,540,868 B2 | | 6/2009 | Elliott et al. |
| 2005/0222581 A1 | | 10/2005 | Fischer et al. |
| 2006/0247699 A1 | | 11/2006 | Burnes et al. |
| 2009/0275926 A1 | | 11/2009 | Liu et al. |

FOREIGN PATENT DOCUMENTS

| | | |
|---|---|---|
| WO | WO 94/08638 | 4/1994 |
| WO | WO 2007/098765 | 9/2007 |

OTHER PUBLICATIONS

Cyberwand Dual Ultrasonic Lithotripter—catalog copyright date 2006.
Cyberwand Dual Probe Ultrasonic Lithotripter System—Rev 00 date unknown.
EMS Product Catalog—Mar. 2008 Edition.
EMS Swiss Lithopump Catalog—Sep. 2007.
LMA Stonebreaker IFU copyright 2008.
LMA Stonebreaker brochure copyright 2006.
International Preliminary Report on Patentability dated Jul. 1, 2010 for related application PCT/US2008/087330.

* cited by examiner

VACUUM ASPIRATION HANDLE

CROSS-REFERENCE TO RELATED APPLICATIONS

This application claims priority from U.S. Provisional Application No. 61/015,004, filed on Dec. 19, 2007, the entirety of which is fully incorporated by reference herein.

BACKGROUND

Often it is desired to remove liquids or particulate matter from a desired location within a patient, either through an orifice in the patient or percutaneously. Various methods of removal are known in the art, from direct removal during percutaneous surgery, or with a medical device, such as forceps, a grasper, a snare, a basket or other structures that can be introduced to a specific location within the patient. In some embodiments, the medical device may be positioned within the patient with use of an endoscope, or through a sheath disposed to orient and maneuver the medical device to the desired location. The medical device can then be manipulated by the physician to obtain and retract the particulate matter from the patient.

A disadvantage of removal using a medical device in this manner is that if multiple particulates are desired to be removed, the physician often must serially remove portions of the particulate matter by sequentially inserting and positioning the device, obtaining a portion of the particulate matter in conjunction with the device, fully removing the device and particulate matter from the patient, and then reinserting and repositioning the device to capture and remove additional particulate matter. This serial, repeated process takes a significant amount of time, which makes medical procedures less efficient, causes additional complications, and is generally disadvantageous. Further, this method is often not suitable for removing fluids from within the patients, only particulate matter.

It is known to remove particulate matter and/or fluids from a patient by inserting a sheath or other conduit with a lumen formed therein to a desired location within a patient, which can provide for fluid communication between the desired location and a source of suction, either continuously or periodically. While this method may be an improvement over removal methods using a medical device to mechanically remove particulate matter from a patient, it is often difficult, tedious, and time consuming to selectively allow and prevent suction communication through the conduit.

BRIEF SUMMARY

The present invention provides a medical device. The medical device includes a sheath with an extended distal end portion, a proximal end portion, and a lumen defined therethrough and a handle that is fixedly connected to the proximal end portion of the sheath. The handle includes an operator that is translatable between a first position and a second position. A flow path is defined within the handle in fluid communication with the proximal end portion of the sheath, wherein the operator is configured to substantially block the flow path in a second position and allow flow therethrough in a first position. The flow path additionally includes a portion that is configured to communicate with a remote source of suction. The handle additionally includes a second inlet portion that is configured to receive a tool therethrough and allow the tool to extend through the lumen of the sheath.

The present invention additionally provides an apparatus for communicating a source of suction to a patient. The apparatus includes a sheath extending from a handle to a distal end portion, and a first lumen extending therethrough. The handle includes an internal flow path in fluid communication with the first lumen and a trigger movable between a first position allowing fluid flow through the internal flow path and a second position substantially preventing fluid flow through the internal flow path. The handle additionally is configured to be connected to an external suction source.

The present invention additionally provides a method for removing fluid and particulate matter within a patient. The method includes the steps of inserting a sheath within a patient such that a distal end portion of the sheath is proximate a volume of fluid or particulate matter intended for removal, and operating a handle constrained with and in fluid communication with the sheath through an internal flow path defined within the handle. The method additionally includes the steps of connecting a remote source of suction to the internal flow path within the handle to allow suction flow through the internal flow path and a first lumen defined within the sheath and controlling the flow of suction through the internal flow path with a controller disposed upon the handle.

Advantages of the present invention will become more apparent to those skilled in the art from the following description of the preferred embodiments of the invention that have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE DRAWINGS AND THE PREFERRED EMBODIMENTS

Figure 1:
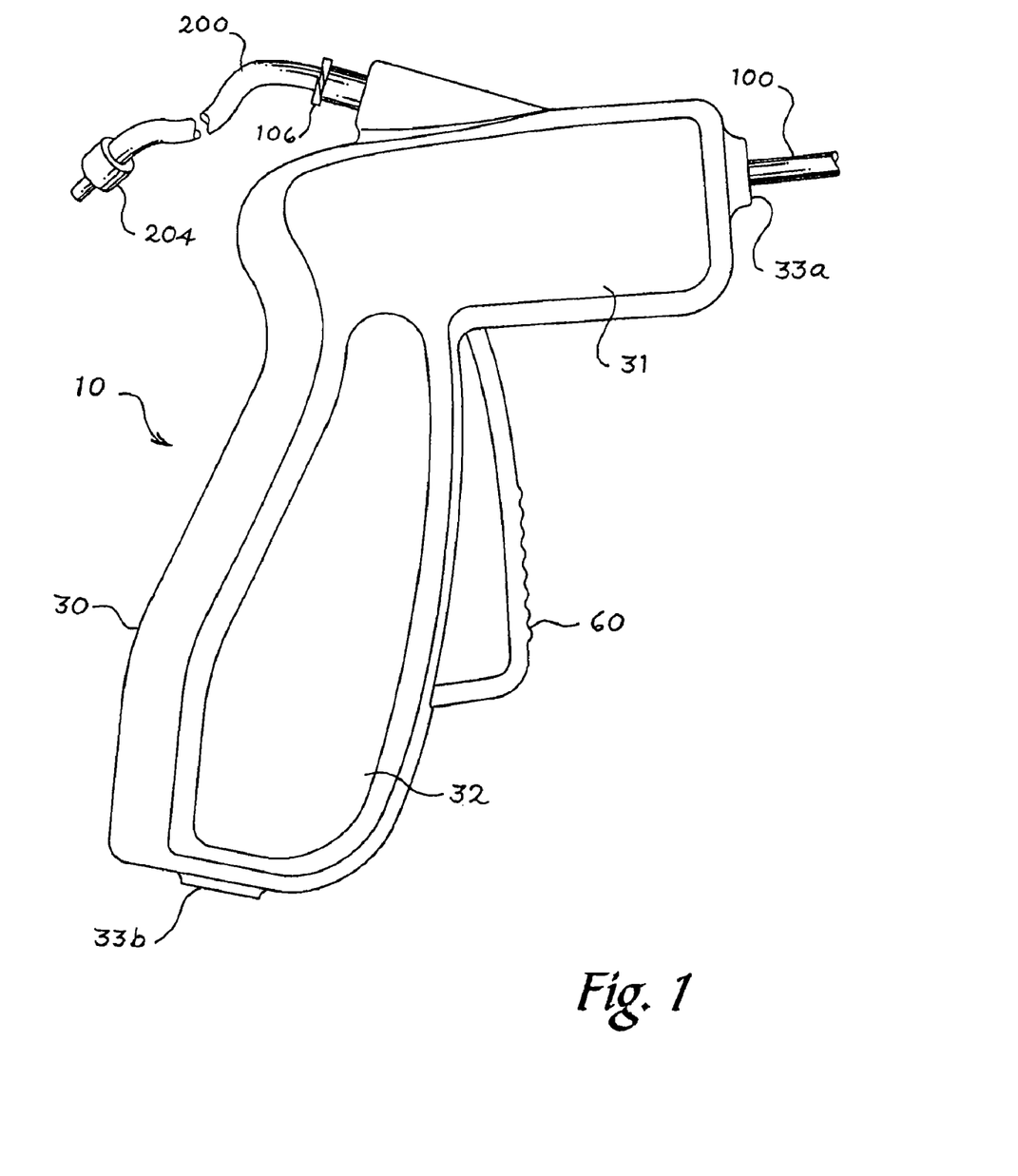
FIG. 1 is a perspective view of a suction device.
Figure 2:
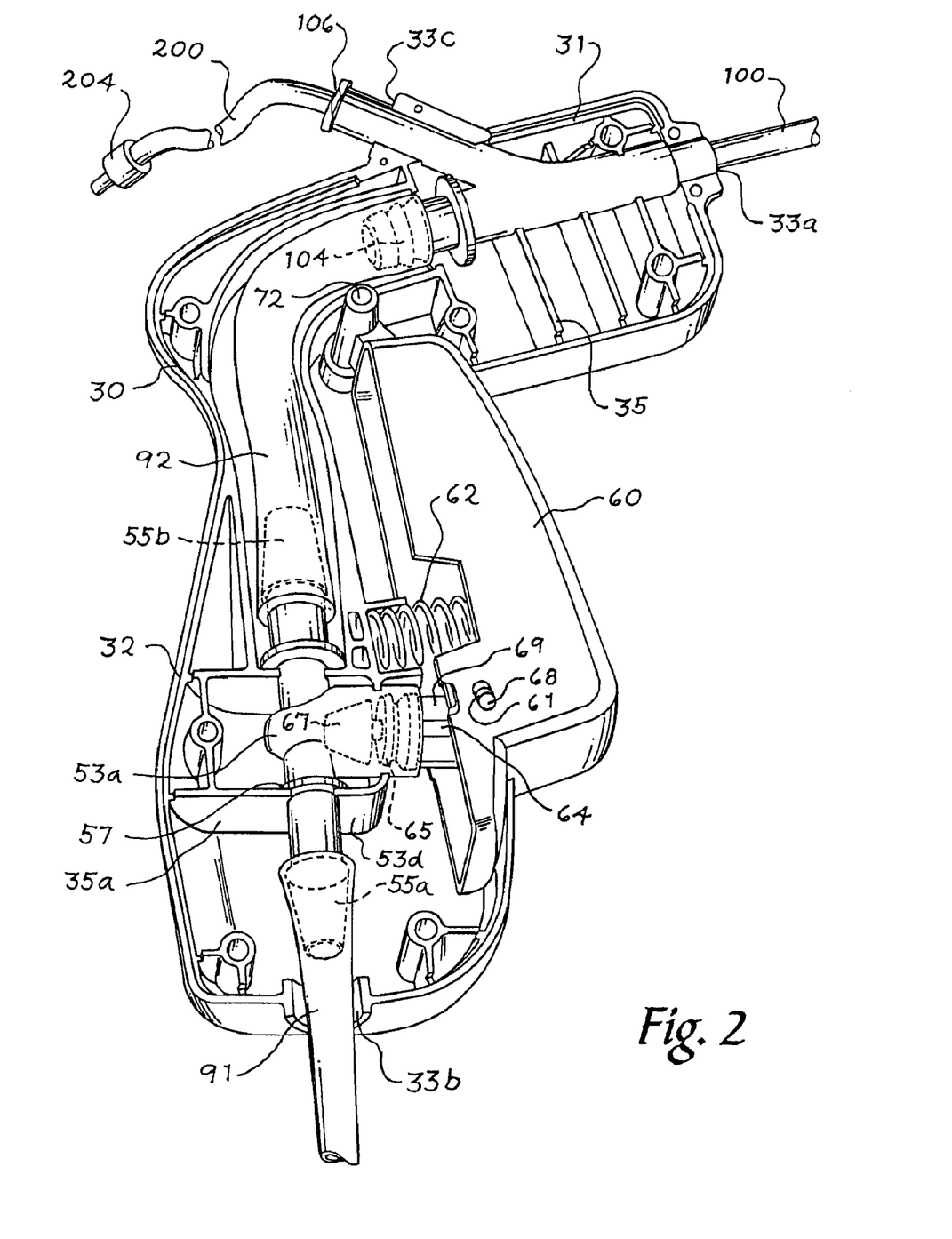
FIG. 2 is an internal view of the suction device of FIG. 1 disposed in a first position.
Figure 3:
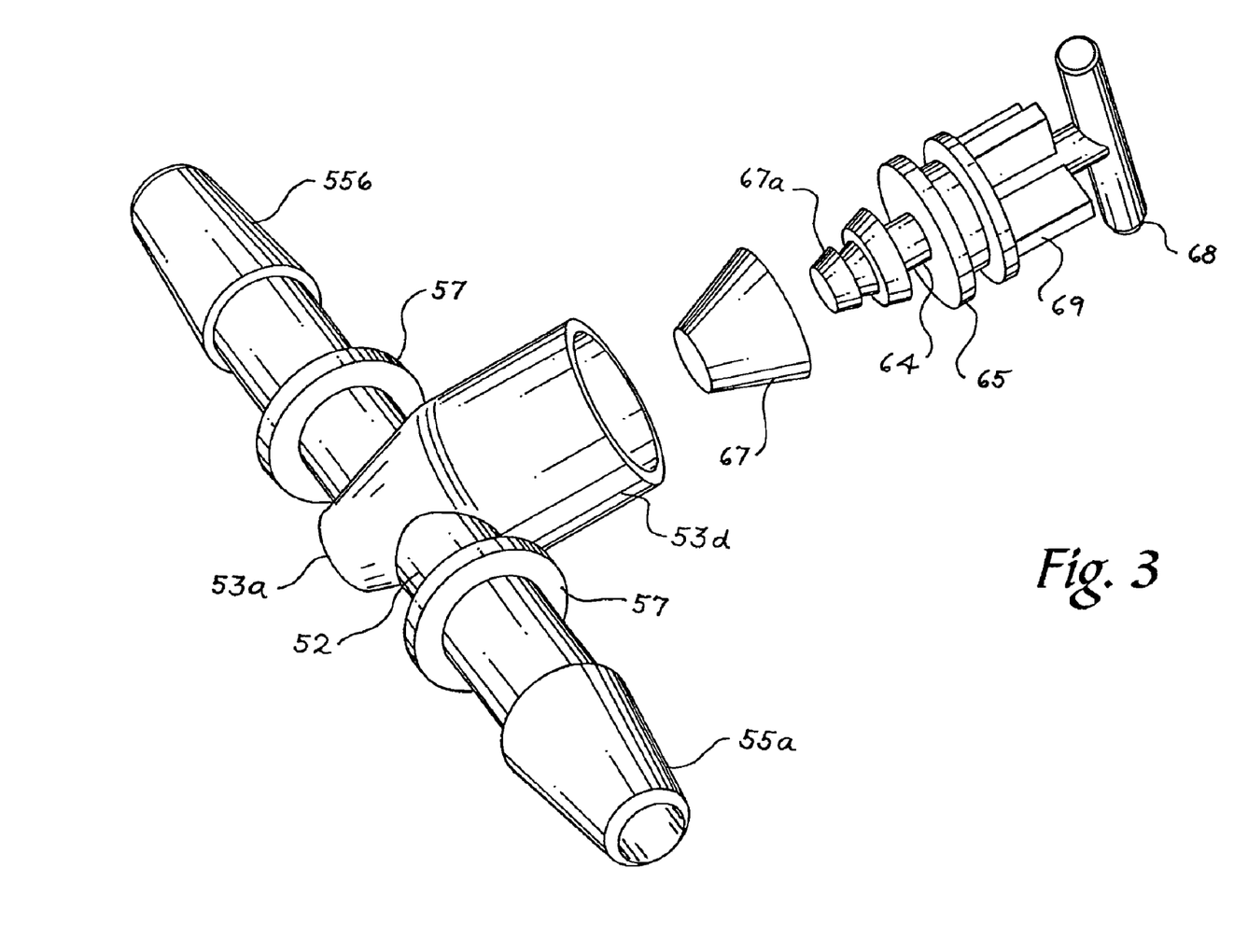
FIG. 3 is an exploded view of a portion of the components of the suction device of FIG. 4.

Turning now to FIGS. 1-3, a suction device 10 is provided. The suction device 10 includes a handle 30, a sheath 100 that extends therefrom, and a trigger 60 or other operator that selectively controls fluid flow through the device 10. The device 10 may additionally be configured to attach to a remote suction system (not shown) through a connector disposed on a first end 55a of an internal flow path 50 that allows fluid communication of the suction forces provided by the remote suction system through handle 30 and ultimately through the sheath 100. The trigger 60 is provided to allow a user to selectively block the suction flow through the handle 30 of the device 10.

The handle 30 may be configured with a pistol shape, with the trigger 60 movably disposed upon a gripping portion 32 of the housing 30 and the sheath 100 extending from the barrel portion 31 of the handle 30. The trigger 60 is pivotally disposed upon the gripping portion 32 of the handle 30 and is configured to be controlled by the user's fingers that wrap around the gripping portion 32, in a motion similar to that used when pulling the trigger of a pistol-style firearm.

The handle 30 includes a first aperture 33a defined at the front end of the barrel portion 31, which provides an opening in the handle 30 for the sheath 100 to extend outwardly from the handle 30. The handle 30 further includes a second aperture 33b defined within or at the bottom end of the gripping portion 32 of the handle 30 to receive or allow physical communication with a hose or other conduit to provide fluid communication between an external source of suction and the internal flow path 50. In some embodiments, the handle 30 may additionally include a third aperture 33c that is defined upon the barrel portion 31, which provides an aperture for receiving or allowing physical communication with a second port 106 of a sheath 100. As discussed below, the second port 106 is aligned on the sheath 100 to allow communication through a second lumen 114 of a sheath 100 configured with dual parallel lumens 112, 114 defined therewithin.

The handle 30 may be constructed from two or more clamshell halves that may rigidly mounted together with fasteners, such as screws or rivets, to define and fix the outer ergonomic surfaces of the handle 30. The barrel portion 31 of the handle 30 may include a plurality of ribs 35 or other structures for retaining and supporting an internal proximal portion 101 of the sheath 100 disposed within the handle 30. Further, the gripping portion 32 of the handle 30 may include two parallel and separated second ribs, or retaining walls 35a defined to support the housing portion 52 of the internal flow path 50. Specifically, the second ribs 35a each define apertures 35b (when the two opposing clamshell halves are rigidly connected) that have a smaller diameter than a pair of washers 57 disposed on opposite sides of the flow path housing 52. The flow path housing 52 is disposed within the handle 30 such that the washers 57 are each disposed proximate to and outside of the neighboring second ribs 35a to fix the flow path housing 52 within the handle 30. The washers 57 may be formed monolithically with the remainder of the flow path housing 52, or may be separate components and fixed to the flow path housing 52.

The handle 30, and specifically the gripping portion 32, pivotably retains the trigger 60. The trigger 60 is rotatably mounted to the handle 30 with a rotating pin 72 that is received within a boss 39 defined within one or both of the clamshell halves that define the handle 30. The trigger 60 is biased outward away from the gripping portion 32 into the first position (as best shown in FIGS. 1 and 2) by a spring 62 that is disposed between the gripping portion 32 and the trigger 60. As discussed in more detail below, movement of the trigger 60 between the first and second positions alters the position of the valve seat 67 within the flow path housing 52, which controls the ability or magnitude of fluid flow through the internal flow path 50 within the device 10. The trigger 60 may be rotated to the second position, shown in FIG. 4, which causes the valve seat 67 to substantially block fluid flow through the internal flow path 50 within the device 10. The trigger 60 is normally rotated by the user by compressing the trigger 60 toward the gripping portion 32 of the handle 30 against the outward biasing force of the spring 62.

The movement of the trigger 60 causes similar translation of the valve seat 67 due to the combined operation of a first pin 64 and a second pin 68 that are each constrained to move with the trigger 60. The first pin 64 extends rearwardly from the valve seat 67, along a line collinear with a central axis of the valve seat 67. The first pin 64 may include or fixedly support a plunger 65 defined between the valve seat 67 and the second pin 68. The plunger 65 is formed with substantially the same outer diameter as the inner diameter of a conical portion 53d of the flow path housing 52. The plunger 65 provides a barrier to enclose the conical portion 53d to substantially prevent fluid or gaseous leakage from, or fluid or gaseous intake into, the flow path housing 52 through the conical portion 53d. The first pin 64 may additionally include a plurality of ribs 69 defined thereon, which provide additional structural support for the plunger 65 and the first pin 64. In some embodiments, the gripping portion 32 may include one or more tracks defined therein which receive one or more of the plurality of ribs 69 to constrain the motion of the first pin 64 within the gripping portion 32.

The first pin 64 is connected (either monolithically or integrally) with the second pin 68. In some embodiments, the first and second pins 64, 68 may be aligned at substantially perpendicular angles with respect to each other. One or both of the ends of the second pin 68 extend through apertures 61 in the trigger 60 to cause the second pin 68 to translate when the trigger 60 is rotated with respect to the gripping portion 32 and against (or with) the biasing force of the spring 62. In other embodiments, the second pin 68 may be retained and moved by the trigger 60 using other structures, such as one or more bosses within the trigger 60. As the second pin 68 translates, the first pin 64 and the valve seat 67 additionally translate within the flow path housing 52 as guided by the conical portion 53d and the base 53a of the flow path housing 52. In embodiments with the ribs 69 provided upon the first pin 64, the translation of the first and second pins 64, 68, and the valve seat 67 is additionally guided by the sliding contact between the plurality of ribs 69 and the tracks formed on the gripping portion 32.

In some embodiments, the valve seat 67 may be monolithically formed upon the first pin 64. In other embodiments best shown in FIG. 3, the valve seat 67 may be connected to a receipt portion 67a of the first pin 64, allowing the valve seat 67 to be formed from a different material as the first pin 64. In some embodiments, the valve seat 67 may be formed from rubber, silicone, or another relatively elastic material that allows the valve seat 67 to deform as necessary when contacting the base 53a of the flow path housing 52 (when the trigger 60 is rotated to the second position shown in FIG. 4). The deformation of the valve seat 67 provides a substantially leak-tight connection between the valve seat 67 and flow path housing 52 to substantially eliminate the flow through the internal flow path 50.

In other embodiments an operator may be provided to selectively allow fluid or gaseous communication through the flow path housing 52. For example, the operator may be a sliding member that is movably retained upon the gripping portion 32 of the handle 30 and movable between first and second positions. The operator may fixably receive a first pin, which may be fixed to a second pin that causes motion of the valve seat within the valve housing, similar to the embodiment discussed above. The operator may be biased to the first position to allow flow through the flow path housing, and translatable to a second position where the valve seat contacts the base within the flow path housing to substantially prevent fluid or gaseous flow through the flow path housing. In still other embodiments, an operator may be a lever, or a pivotable member that is movable between multiple positions that ultimately controls the motion of a valve seat to control the flow through the valve housing and the device.

Figure 6:
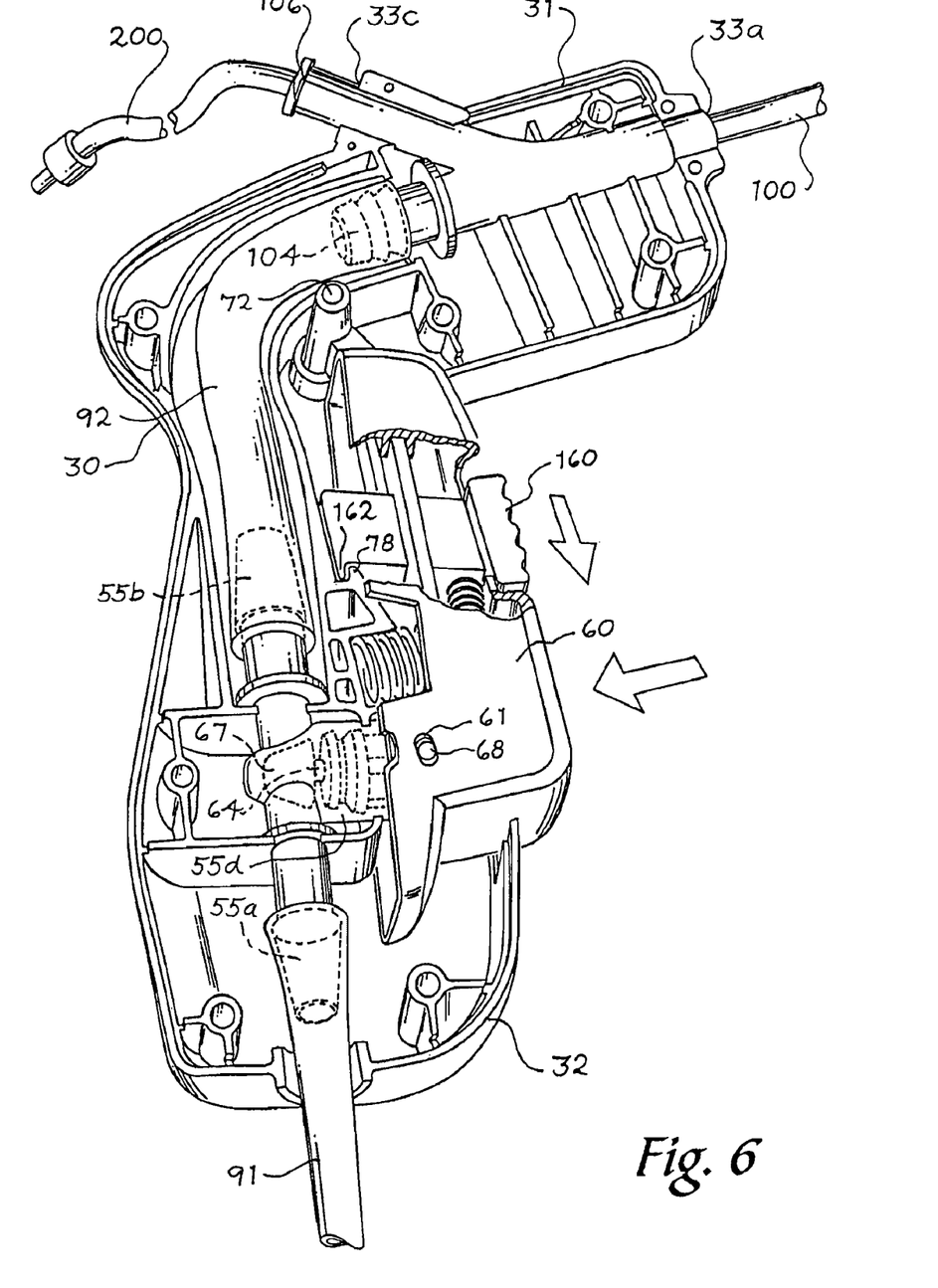
FIG. 6 is an alternate view of the suction device with a lock.

In some embodiments shown in FIG. 6, the trigger 60 may be retained at the second position by a lock 162 disposed upon the handle 30 (and specifically upon the trigger 60 or the gripping portion 32 of the handle 30), which releasably prevents the trigger 60 from rotating toward the first position due to the outward biasing force of the spring 62. The lock 162 may be a tab that is selectively extended into a recess 164 in the trigger 60 when the trigger 60 is in the second position, as shown in FIG. 6. The lock 162 may be translated upward and downward with respect to the trigger 60 by a lock handle 160. The lock handle 160 is fixed to the handle 30 with a first leg 172 that is received through a first slot 168 in the lock handle 160. The lock handle 160 may be nested within an aperture in the trigger 60 and slidably constrained to the trigger 60 with a second leg 166 that is fixed to the trigger 60 and slidably received within a second slot 167 in the lock handle 160. Accordingly, the lock handle 160 can translate with respect to the trigger 60, such that the lock 162 extends within a port 164 in the trigger 60 to retain the trigger 60 in the second position. The lock 162 may be disengaged from the port 164 in the trigger 60 by pulling the lock handle 160 upward with respect to the trigger 60, which allows the trigger 60 to return to the first position due to the biasing force of the spring 62.

In other embodiments, the lock 162 may be a sliding member retained upon the gripping portion 32 that can be translated with respect to the gripping portion 32 when the trigger 60 is in the second position to mechanically block the trigger 60 from rotating to the first position. In other embodiments, the lock 162 may be different structures that are configured to retain the trigger 60 in the second position.

The internal flow path 50 through the handle 30 is best shown in FIGS. 2 and 3. The internal flow path 50 includes the flow path housing 52 normally disposed within the gripping portion 32 and one or more fluid conduits disposed within the handle 30 to fluidly connect the first port 104 of the sheath 100 with the flow path housing 52 and to fluidly connect the flow path housing 52 with the remote source of suction. The flow path housing 52 is a substantially rigid member that includes opposed first and second ends 55a, 55b, a base 53a disposed therebetween, and a conical portion 53d that is disposed proximate to and extending away from the base 53a. The first end 55a is configured to connect with a remote source of suction (either directly or through an intermediate conduit 91 connected with the first end 55a) to allow the flow path housing 52 to fluidly communicate with the remote source of suction. The conduit 91 connecting the first end 55a of the flow path housing 52 extends through the second aperture 33b defined at the bottom of the gripping portion 32.

The second end 55b of the flow path housing 52 is configured to be fluidly connected with the first port 104 of the sheath 100 with a conduit 92 disposed within the housing 30. The conduit 92 may be a flexible tube such as tygon tubing or the like. The base 53a of the flow path housing 52 is configured to receive the valve seat 67 when the trigger 60 is pivoted to the second position. Specifically, the base 53a of the flow path housing 52 is disposed between the first and second ends 55a, 55b of the flow path housing 52, and the valve seat 67 of the trigger 60 is received therein to block the flow of fluid or gas between the first and second ends 55a, 55b. The base 53a of the flow path housing 52 may be conical to receive similarly conically shaped and sized valve seat 67. In other embodiments both the valve seat 67 and the base 53a of the flow path housing 52 may be cylindrical or formed with other similar sizes and shapes.

As discussed above, the first and second ends 55a, 55b each include a washer 57 defined thereon, with each of the washers on the flow path housing 52 disposed on opposing outer surfaces of two opposite second ribs 35a to fix the flow path housing 52 with respect to the gripping portion 32 of the handle 30. In some embodiments, each of the first and second ends 55a, 55b of the flow path housing 52 may be configured to form a conical shape, such as a hose barb, to retain the respective conduit 91, 92 thereon. The hose barb includes an increasing outer diameter from the end portion toward the base 53a, with the largest diameter of the barb being larger than the inner diameter of the respective conduit 91, 92 used to connect with the barb and the flow path housing 52. Specifically, as the hose barb is inserted into a lumen of the conduit, the inner of the conduit eventually contacts the hose barb and with further longitudinal movement along the barb expands the diameter of the lumen within the conduit. With sufficient expansion, a large frictional force is developed between the hose barb and the conduit 91, 92, which retains the conduit 91, 92 upon the hose barb.

Figures 5, 9:
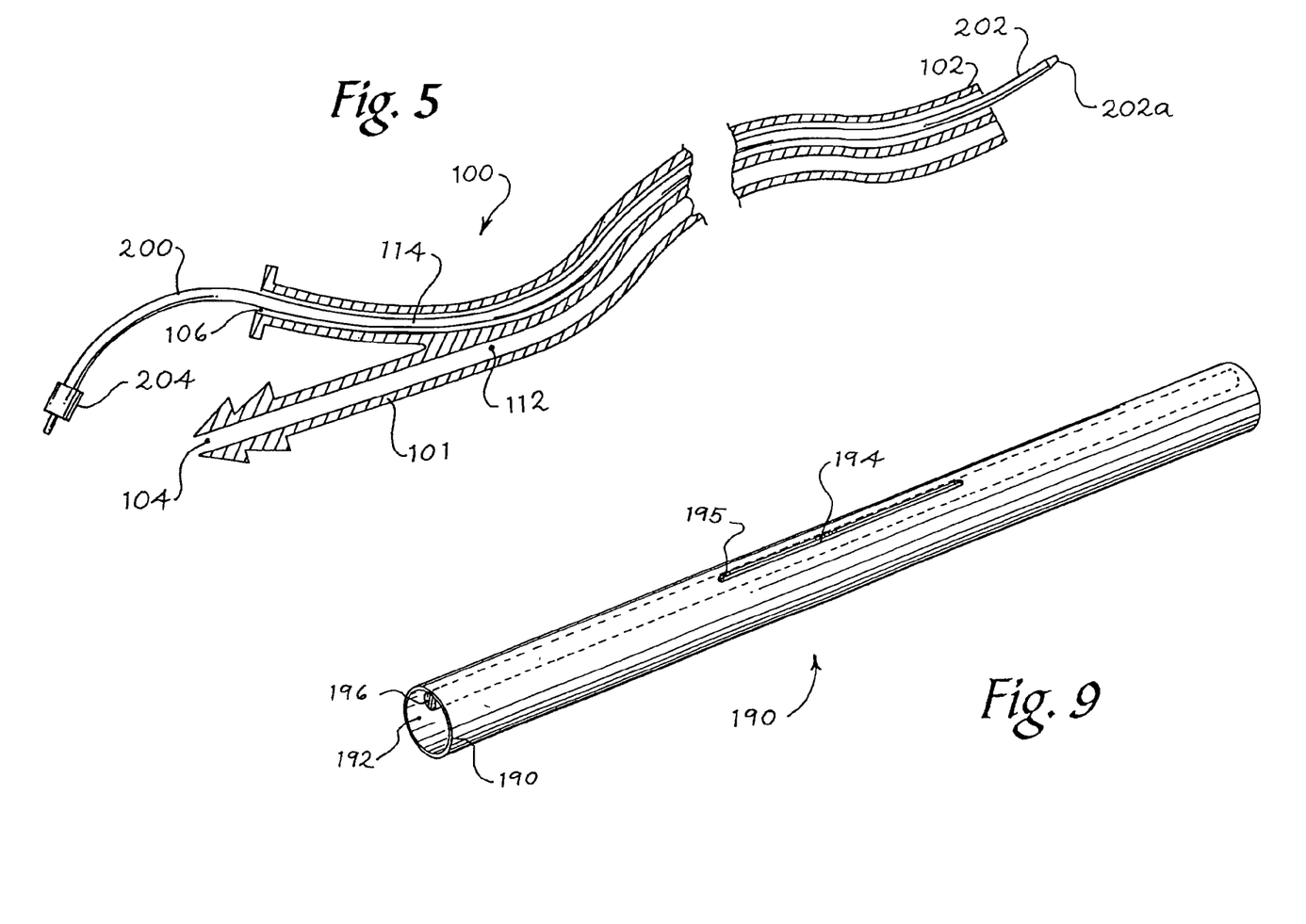
FIG. 5 is a cross-sectional view of the sheath of the suction device of FIG. 1.
FIG. 9 is a perspective view of an alternate sheath usable with the suction device of FIG. 1.

The sheath 100 is best shown in FIGS. 2 and 5. Specifically, the sheath 100 includes first and second ports 104, 106 that each provide for fluid or mechanical communication with first and second lumens 112, 114, respectively, which are defined along the length from the proximal end portion 101 of the sheath 100 to the distal end portion 102 that projects from the handle 30. The sheath 100 is configured to be similar to that disclosed in pending U.S. Published Application No. 2005/0222581, titled "Multiple Lumen Access Sheath," filed on Mar. 24, 2005, and commonly assigned to the assignee of this pending application, the entirety of which is fully incorporated by reference herein. In some embodiments, the sheath 100 may be a relatively flexible material, or composite material. In other embodiments, the sheath 100 may be a less flexible material, such as stainless steel.

In some embodiments, the first port 104 and the first lumen 112 are configured for providing fluid communication between the remote suction source and the first lumen 112 (though the first and second conduits 91, 92 and the flow path housing 52) to allow communication of the suction to the patient proximate to the distal end portion 102 of the sheath 100. The first port 104 and first lumen 112 are each sized to enable fluid and some particulate matter (i.e. with a cross-section smaller than the internal diameter of the first lumen 112) entrained therewith to enter the first lumen 112 of the sheath 100 and eventually flow through the length of the sheath 100, the first and second conduits 91, 92, the flow path housing 52 and ultimately out of the device 10 toward the remote suction source.

The second port 106 and second lumen 114 are each configured to provide a second independent path between the distal end portion 102 of the sheath 100 and the handle 30. The second port 106 may be oriented at an angle of about 20 degrees with respect to the longitudinal axis of the sheath 100 leaving the handle 30. In some embodiments, the inner diameter of the second lumen 114 is significantly smaller than the inner diameter of the first lumen 112, in order to allow a relatively large first lumen 112, while minimizing the overall outer diameter of the sheath 100.

In some embodiments, the inner diameter of the first lumen 112 may be about 9.5 Fr, 10 Fr, 12 Fr, or 14 Fr, while the inner diameter of the second lumen may be about 3 Fr. The second lumen 114 (and second port 106) are configured to allow a plurality of tools, such as elongate medical devices and laser fibers to extend therethrough, from the handle 30 (by way of the third aperture 33c in embodiments where the port 106 is located within the internal volume of the handle 30) to exit the distal end portion 102 of the sheath 100. For example, a laser fiber 200 may be threaded through the second port 106 and through the second lumen 114 to extend from the sheath 100 at the desired location within the patient. The laser fiber 200 may then be used to break or ablate stones, calcified material, or other particulate matter within the patient, which is too large to enter the first lumen 112 of the sheath 100.

In some embodiments shown in FIG. 9, an alternate sheath 190 may be provided. The sheath 190 includes a first lumen 192 that is configured to fluidly connect with the flow path housing 52. The sheath 190 additionally includes a second lumen 194 that is disposed within (or proximate) the inner diameter of the first lumen 192, with the portion of the walls forming the first lumen 192 and the second lumen 194 being fixed together, or supported together in concert or close proximity. The second lumen 194 includes an elongate slot 195 that is defined within a side surface of the second lumen 194 and a side surface of the first lumen 192. The slot 195a allows for a gradual continuous bend of the laser fiber 200 as it enters the second lumen 194 from the second portion 106 of the handle 30. The second lumen 194 is blocked at the proximal end of the sheath 190 to prevent suction from the internal flow path 52 from traveling to the second port, which maintains the vacuum within the first lumen 192 within acceptable levels. The sheath 190 may be stainless steel or alternatively more flexible materials, or composite materials.

The laser fiber 200 may be a separate component from the sheath 100 and may be configured to be threaded through the second port 106 and through the second lumen 114 to extend through the distal end 101 of the sheath 100 by the physician immediately before, or during the medical procedure. In other embodiments, the laser fiber 200 may be provided pre-threaded through the second port 106 and second lumen 114 when the device 10 is purchased and readied for use in a patient.

The laser fiber 200 includes a distal end 202 that defines a tip 202a from which a laser beam is released and a proximal end 204 which forms a plug which is suitable for connecting and receiving a laser signal or laser beam from a remote laser generator. The laser fiber 200, specifically the distal end 202 and the central portion 205 may be a 3 Fr laser fiber 200 to allow the laser fiber 200 to be threaded through the second port 106 and the second lumen 114 of the sheath 100 that extends from the handle 30.

The distal end 202 receives energy and produces a laser beam, or alternatively, receives a laser beam transmitted through the laser fiber 200 from the laser generator and directs the laser beam toward the tissue or particulate matter proximate and in-line with the tip 202a of the distal end 202 of the laser fiber 200. The laser beam imparts energy to the tissue or particulate matter proximate and in-line with the distal end 202 to break up or ablate the tissue or particulate matter into smaller chunks or pieces. In some embodiments, the distal end 202 of the laser fiber 200 may be used to break or ablate stones in the patient's kidney. The small broken or ablated pieces or chunks then may be pulled or vacuum dragged into the first lumen 112 of the sheath 100 due to the presence of suction from the communicated from the first lumen 112 to remove the tissue or particulate matter from the patient.

In other embodiments, medical tool, such as a grasper, basket, snare, forceps, or the like that is smaller than the about 3 Fr inner diameter of the second lumen 114 to allow the medical tool to be inserted through the second port 106 and threaded through the second lumen 114 to remove particulate matter from a patient or obtain a tissue sample, such as a biopsy, from a patient. In embodiments where the medical tool is used, the laser fiber 200 (when provided) is withdrawn from the second lumen 114 and the second port 106 to allow room for the medical tool to be inserted into the second port 106 and the second lumen 114.

In use, the suction device 10 is operated in the following manner. The sheath 100 may be inserted into the patient through one of many convenient orifices within the patient (such as the urethra) or the sheath 100 may be inserted into the patient percutaneously. In some embodiments, the sheath 100 may be inserted into the patient through a lumen in an endoscope and correctly positioned within the patient with the use of a camera or similar viewing device provided with the endoscope. After the device 10 is inserted, the distal end portion 102 of the sheath 100 is correctly positioned within the patient by the physician.

After the distal end portion 102 of the sheath 100 is correctly positioned within the patient, the physician manipulates the laser fiber 200 to break-up or ablate the issues, stones, or particulate matter proximate and in-line with the tip 202a of the laser fiber 200. When the tissue, stones, or particulate matter is sufficiently ablated, the physician attaches or inserts a remote source of suction (normally provided by the medical facility) into the second aperture 33b in the handle 30 and connects the source of suction to the first end 55a of the flow path housing 52. With the source of suction fluidly connected with the flow path housing 52 and the trigger 60 at the first position (FIG. 2), the source of suction is free to fluidly communicate through the flow path housing 52, the second conduit 92, and the first lumen 112 of the sheath 100. As the suction force reaches the distal end portion 102 of the sheath 100, any liquid, and sufficiently small particulate matter proximate the distal end portion 102 of the sheath 100 is urged into the first lumen 112 and ultimately flows out of the sheath 100 and the handle 30 toward the suction source.

Figure 4:
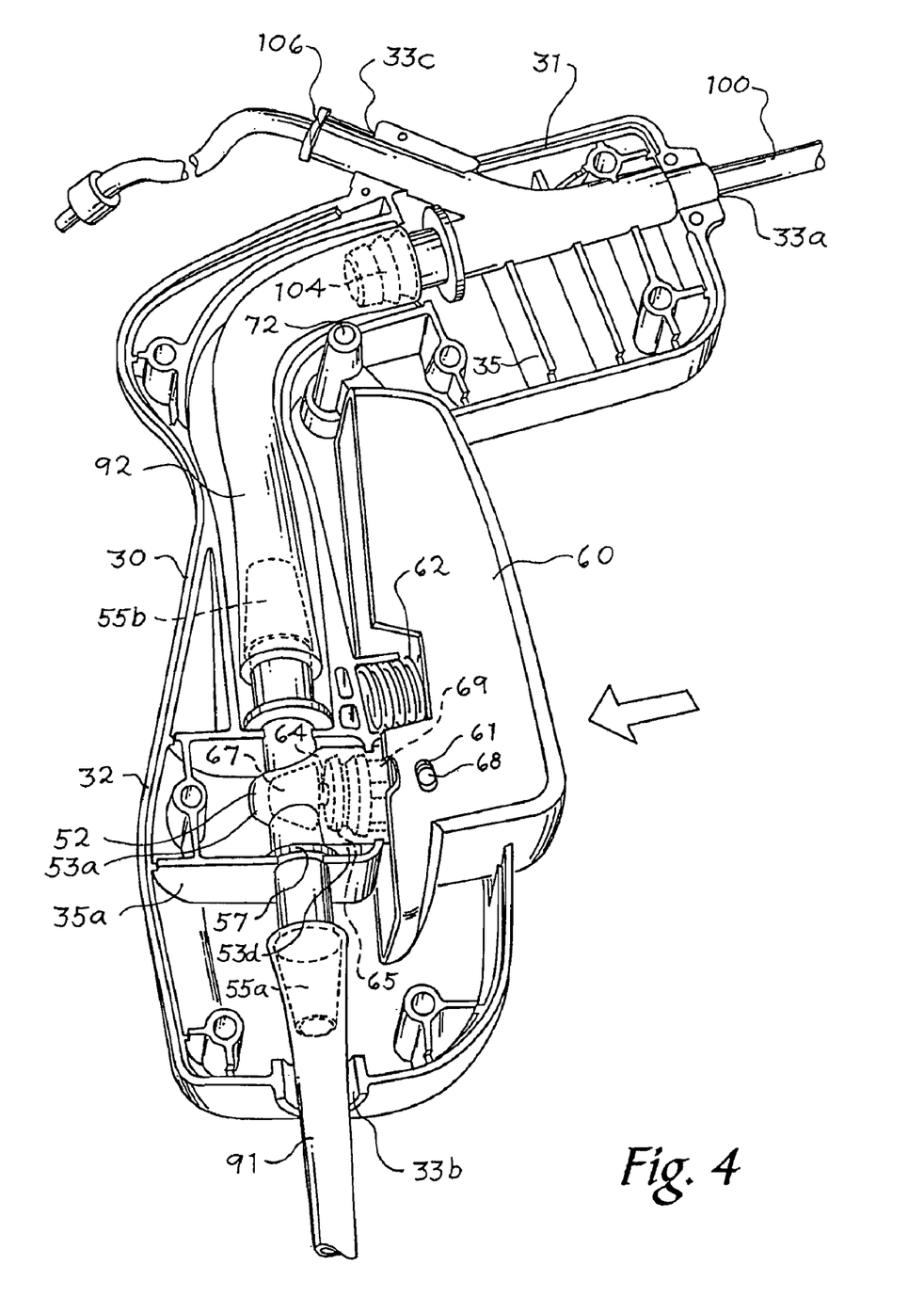
FIG. 4 is the view of FIG. 2 showing the suction device in a second position.

If the physician desires to prevent the suction flow through the handle 30 and the sheath 100 (and therefore prevent liquid and particulate flow through the sheath 100 and handle 30), the user may compress the trigger 60 toward the second position (FIG. 4). As the trigger 60 is urged toward the gripping portion 32, the first and second pins 64, 68 are similarly translated inward until the valve seat 67 disposed on the first pin 64 contacts the base 53a of the flow path housing 52. This contact causes the valve seat 67 to substantially block the flow path housing 52 and prevent fluid or gaseous flow or communication between the first and second ends 55a, 55b of the flow path housing 52. As the gaseous and fluid flow is substantially blocked, the suction force is no longer communicated through the first lumen 112 of the sheath 100 and to the volume proximate the distal end portion 102 of the sheath 100. The physician may selectively retain the blockage of the suction flow through the flow path housing 52 by translating the locking handle 160 to insert the lock into the trigger 60, or by implementing other mechanical locks discussed herein to retain the trigger 60 in the second position. When the physician desires to restore the suction flow through the flow path housing 52, the physician disengages the lock 162 from the trigger 60, allowing the trigger 60 to return to the first position due to the outward biasing force of the spring 62.

In addition to selectively communicating the source of suction through the first lumen 112, the physician may continue to selectively operate the laser fiber 200 in conjunction with suction flowing through the first lumen 112 of the sheath 100. The laser fiber 200 laser may continue to break or ablate stones, calcium deposits, or other particulate matter, which is too large to enter the first lumen 112, to obtain particulate matter sized to be withdrawn through the first lumen 112 of the sheath 100 in the presence of the source of suction communicated through the first lumen 112.

In other embodiments, a medical tool, such as a grasper, forceps device, snare, basket, or the like that has an outer diameter smaller than the inner diameter of the second lumen 114 can be inserted through the second port 106 and the second lumen 114 to selectively manipulate tissue or particulate matter proximate the distal end 101 of the sheath 100. The medical tool may be manipulated to remove relatively small particulate matter or obtain tissue samples from the patient proximate the distal end portion 102 of the sheath 100.

In some embodiments, the laser fiber 200 may be initially used to ablate the particulate matter proximate the distal end 102 of the sheath and then withdrawn from the second lumen 114. The medical tool may then be inserted through the second port 106 and the second lumen 114 to obtain and remove a sample of the tissue or particulate matter for analysis. Further suction force may be selectively communicated through the first lumen 112 to the area proximate the distal end 152 of the sheath to selectively remove particulate matter and tissue from the patient proximate the distal end 101 of the sheath 100. While the laser fiber 200 is used to ablate the tissue and particulate matter and the medical tool is used to remove and retain a portion of the particulate matter for analysis, the suction flow may be secured (by translating the trigger 60 to the second position, and if desired retaining the trigger 60 in the second position with the lock 162).

Figure 7:
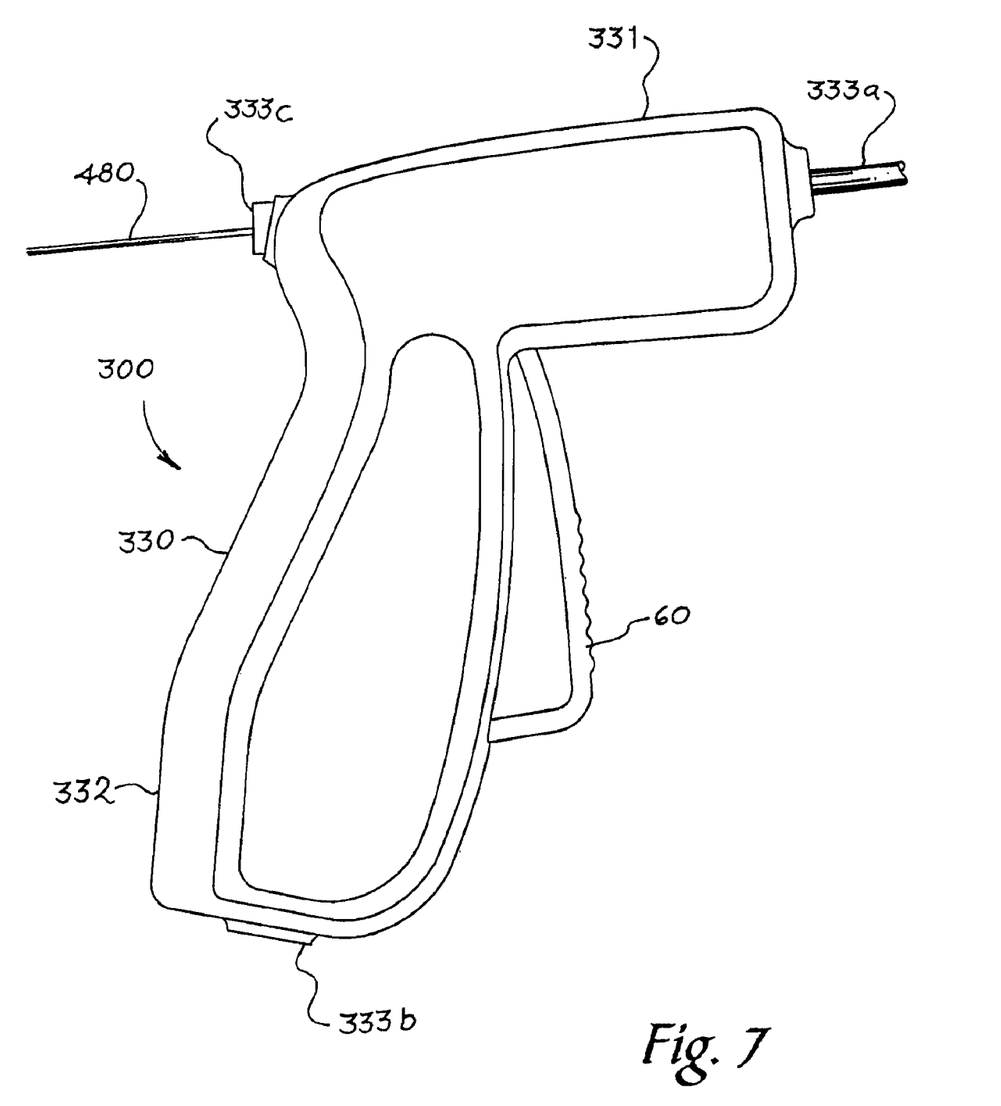
FIG. 7 is a perspective view of another suction device.
Figure 8:
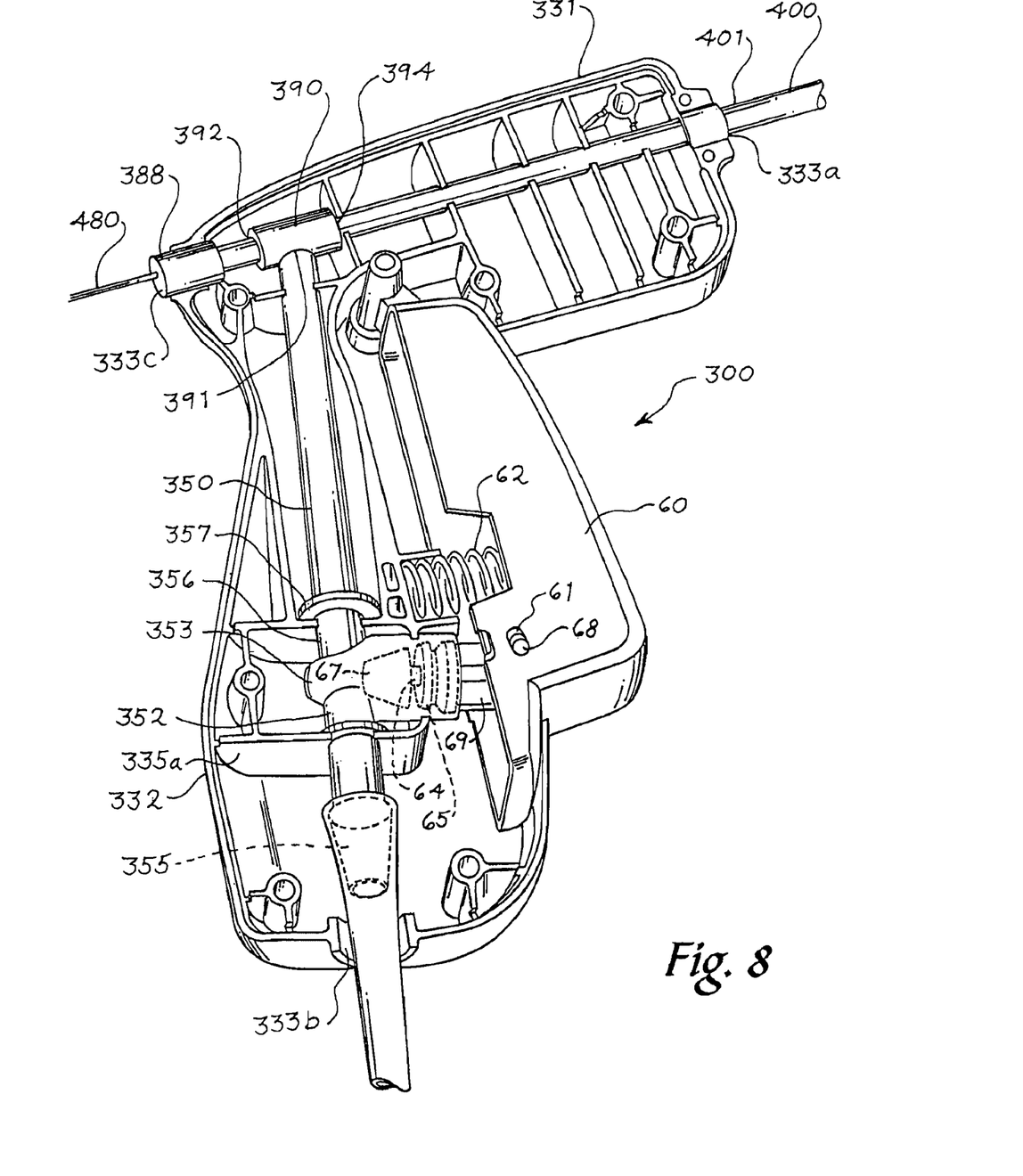
FIG. 8 is an internal view of the suction device of FIG. 7 disposed in a first position.

Turning now to FIGS. 7-8, an alternate suction device 300 is provided. The suction device 300 is similar to the device 10 discussed above and depicted in FIGS. 1-3. Because of the similarity of many of the components, like element numbers will be used to describe like portions of the suction device 300. The suction device includes a handle 330, a sheath 400 that extends therefrom, and a trigger 60 or other operator that controls fluid (and suction) flow through the device 10. The device 300 may additionally be configured to be attached to a remote suction system (not shown) through a connector disposed on a first end 355a of an internal flow path 350 that allows fluid communication of the suction forces provided by the remote suction system through handle 330 and ultimately through the sheath 400. The trigger 60 is provided to allow a user to selectively block the suction flow through the handle 330 of the device 300. The trigger 60 and associated movement of the valve seat 67 is the same as described with respect to the suction device 10, above.

The handle 330 may be configured with a pistol shape, with the trigger 60 movably disposed upon a gripping portion 332 of the housing 330 and the sheath 400 extending from the barrel portion 331 of the handle 330. The trigger 60 is pivotally disposed upon the gripping portion 332 of the handle 330 and is configured to be controlled by the user's fingers that wrap around the gripping portion 332, in a motion similar to that used when pulling the trigger of a pistol-style firearm.

The handle 330 includes a first aperture 333a defined at the front end of the barrel portion 331, which provides an opening in the handle 330 for the sheath 400 to extend outwardly from the handle 330. The handle 330 further includes a second aperture 333b defined within or at the bottom end of the gripping portion 332 of the handle 330 to receive or allow physical communication with a hose or other conduit to provide fluid communication between an external source of suction and the internal flow path 350. In some embodiments, the handle 330 may additionally include a third aperture 333c that is defined upon the rear end of the barrel portion 331, which provides an aperture for receiving or allowing physical communication with the sheath 400 and the internal flow path 350. As discussed in additional detail below, the third aperture 333c supports a fluid connection with the internal flow path 350, with a T connector 390 or the like that is configured to allow flow from both the second aperture 333b and the third aperture 333c to ultimately reach first aperture 333a and the sheath 400. The third aperture 333c may include a check flow valve 388 or similar structure to allow objects, structures, or forced fluid flow through the aperture 333c into the handle 330, but substantially prevent fluid flow through the aperture 333c out of the handle 330.

The handle 330 may be constructed from two or more clamshell halves that may rigidly mounted together with fasteners, such as screws or rivets, to define and fix the outer ergonomic surfaces of the handle 330. The barrel portion 331 of the handle 330 may include a plurality of ribs or other structures for retaining and supporting an internal proximal portion 401 of the sheath 400 disposed within the handle 330. Further, the gripping portion 332 of the handle 330 may include two parallel and separated second ribs, or retaining walls 335a defined to support the internal flow path 350. Specifically, the second ribs 335a each define apertures (when the two opposing clamshell halves are rigidly connected) that have a smaller diameter than a pair of washers 357 disposed on opposite sides of the flow path housing 52. The internal flow path 350 is disposed within the handle 330 such that the washers 357 are each disposed proximate to and outside of the neighboring second ribs 335a to fix the flow path housing 352 within the handle 330. The washers 357 may be formed monolithically with the remainder of the flow path housing 352, or may be separate components and fixed to the flow path housing 352.

The handle 330, and specifically the gripping portion 332, pivotably retains the trigger 60. The trigger 60 is rotatably mounted to the handle 330 with a rotating pin 72 that is received within a boss 339 defined within one or both of the clamshell halves that define the handle 330. The trigger 60 is biased outward away from the gripping portion 332 into the first position (as best shown in FIG. 7) by a spring 62 that is disposed between the gripping portion 332 and the trigger 60. As discussed in more detail below, movement of the trigger 60 between the first and second positions alters the position of the valve seat 67 within the flow path housing 352, which controls the ability or magnitude of fluid flow through the internal flow path 350 within the device 300. The trigger 60 may be rotated to the second position, similar to the position of the trigger 60 in FIG. 4, which causes the valve seat 67 to substantially block fluid flow through the internal flow path 350 within the device 300. The trigger 60 is normally rotated by the user by compressing the trigger 60 toward the gripping portion 332 of the handle 300 against the outward biasing force of the spring 62.

The movement of the trigger 60 causes similar translation of the valve seat 67 and the accompanying trigger mechanism in the same manner as movement of the trigger 60 controls the position of the valve seat 67 in the embodiments discussed above and shown in FIGS. 2-4 and 6. For the sake of brevity, the description will not be repeated here.

Similar to the device 10 discussed above, in other embodiments an operator may be provided to selectively allow fluid or gaseous communication through the internal flow path 350. For example, the operator may be a sliding member that is movably retained upon the gripping portion 332 of the handle 330 and movable between first and second positions. The operator may fixably receive a first pin, which may be fixed to a second pin that causes motion of the valve seat within the valve housing, similar to the embodiment discussed above. The operator may be biased to the first position to allow flow through the flow path housing, and translatable to a second position where the valve seat contacts the base within the flow path housing to substantially prevent fluid or gaseous flow through the flow path housing. In still other embodiments, an operator may be a lever, or a pivotable member that is movable between multiple positions that ultimately controls the motion of a valve seat to control the flow through the valve housing and the device.

Similar to the device 10 discussed above, the trigger 60 may be retained at the second position by a lock 162 disposed upon the handle 330 (and specifically upon the trigger 60 or the gripping portion 332 of the handle 330), which releasably prevents the trigger 60 from rotating toward the first position due to the outward biasing force of the spring 62, as shown in FIG. 6 and discussed in detail in the embodiment above.

The internal flow path 350 is best shown in FIG. 8. The internal flow path 350 may be formed from a single component monolithically formed, such as molded as a single piece, or multiple components fixed together. The internal flow path 350 is disposed within the gripping portion 332. The internal flow path 350 provides for fluid communication between the second aperture 333b and a first inlet 391 of a T connector 390, with fluid communication through the internal flow path 350 controlled by the trigger 60 and valve 67 as discussed above. The internal flow path includes a base 353, a first end 355, and a second end 356. The base 353 is configured to selectively receive the valve seat 67 when the trigger 60 is depressed, which prevents fluid flow between the second aperture 333b and the first inlet 391 of the T connector 390. When the trigger 60 is released, a spring returns the trigger 60 to the normal extended position which removes the valve seat 67 from the base and allows fluid flow through the internal flow path 350. The internal flow path 350 includes a first end 355a that extends through the second aperture 333b and is configured to connect with a source of suction, such as a central medical source, or the like. The first end 355 may include a barbed or stepped connector for fixedly receiving tygon tubing or other similar conduits thereon.

In some embodiments, the internal flow path 350 includes a T connector 390, while in other embodiments, the internal flow path 350 makes a releasable connection at a first inlet 391 of a T connector 390. The T connector 390 includes a first inlet 391 with direct fluid communication with the base 353, a second inlet 392 that fluidly communicates through the third aperture 333c, and an outlet 394 that receives an outlet sheath 400 thereon that extends through the first aperture 333a in the handle 330. The second inlet 392 of the T connector 390 is fixed, or in communication with, the third aperture 333c. The second inlet 392 may include a check flow adaptor 388 or the like to allow fluid flow, or objects to pass, through the third aperture 333c and into the second inlet 392, but prevent fluid flow and objects to pass out of the handle through the third aperture 333c. In some embodiments, the third aperture 333c and the second inlet 392 are configured to receive a laser fiber 480 therethrough, which passes through the outlet 394 of the T connector 390. The laser fiber 480 is normally insertable through the third aperture 333c and the check flow adapter 388 and removable therefrom. The laser fiber 480 may be any size of conventional laser fibers, such as 150, 200, 273, 365, 550, and 940 microns. In some embodiments, other tools, such as graspers, snares, baskets and the like, may be inserted through the third aperture 333c and second inlet 392 of the T connection 390 and ultimately through the sheath 400 attached to the outlet 394.

The sheath 400 may be an elongate tubular member that is fixed to the handle 330 and specifically the outlet 394 of the T connector 390 to receive flow from the internal flow path 350 as well as communicate with the second inlet 392. The sheath 400 may include a single lumen that is fluidly connected to the outlet 394 of the T connection 394 to receive suction therefrom (through the internal flow path 350 and ultimately from the suction source connected therewith) and additionally receive the laser fiber 480, or other tool, that is inserted through the third aperture 333c and second inlet 392 of the T connection 390, such that the suction and the laser or tool each extend through the distal end of the sheath 400 to communicate with or be used at the work site. In other embodiments, similar to the device 10 discussed above, the sheath 400 may be a dual lumen sheath, similar to sheath 100 or sheath 190, discussed above. In those embodiments, the third aperture 333c would provide direct communication with a lumen configured to receive a laser fiber or tool (i.e. lumens 114, 194), and the internal flow path (similar to the flow path 50 discussed above) would be fluidly connected to the other lumen of the sheath.

The sheath 400 may be formed from stainless steel, a polymer, or other medically acceptable materials. The sheath 400 is sized to be readily received through working channels of conventional endoscopes, such that the device 300 is configured to be used endoscopically. In other embodiments, the sheath 400 may not be limited by an inner diameter of an endoscope working channel where the device 300 is configured to only be used percutaneously.

While the preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A medical device comprising:
   a sheath comprising an extended distal end portion, a proximal end portion, and parallel and segregated first and second lumens defined therethrough;
   a handle fixedly connected to the proximal end portion of the sheath, the handle comprising an operator comprising a trigger pivotably mounted upon the handle that is translatable between a first position and a second position, wherein the trigger is biased into the first position;
   a flow path defined within the handle in fluid communication with the proximal end portion of the first lumen of the sheath, wherein the operator is configured to substantially block the flow path when the trigger is in the second position and allow flow therethrough when the trigger is in the first position, wherein the flow path comprises a first inlet portion that is configured to communicate with a remote source of suction; and
   a second inlet portion configured to receive a tool therethrough and allow the tool to extend through the second lumen of the sheath; and
   a lock slidably disposed upon the handle for selective engagement with the trigger to maintain the trigger in the second position wherein the operator comprises a valve seat that translates with motion of the trigger between the first and second potions, wherein the valve seat rests upon a first pin oriented substantially in the direction of travel of the valve seat, and further comprising a second pin connected with the first pin, the second pin being fixably mounted to the first pin.

2. The medical device of claim 1, wherein the tool is a laser fiber.

3. The medical device of claim 1, wherein the tool is a grasper, snare, forceps, or a basket.

4. The medical device of claim 1, wherein the tool is removable from the second inlet portion and the lumen of the sheath.

5. The medical device of claim 1, wherein the first lumen and the flow path are connected to allow the source of suction to communicate with the distal end portion of the sheath from the extended portion of the flow path.

6. The medical device of claim 1, wherein the flow path further comprises a connector with first, second, and third ports that allow communication between the sheath, the first inlet portion, and the second inlet portion.

7. The medical device of claim 6, where the second inlet portion is disposed substantially collinearly with the proximal end portion of the sheath.

8. The medical device of claim 7, where the second inlet portion comprises a check valve disposed therein to allow entry of the tool into the handle and the first lumen of the sheath, but substantially prevent fluid exit from the second inlet portion.

9. An apparatus for communicating a source of suction to a patient, comprising:
 a sheath extending from a handle to a distal end portion, and a first lumen extending therethrough;
 the handle comprising an internal flow path in fluid communication with the first lumen, and a trigger pivotably movable between a first position allowing fluid flow through the internal flow path and a second position to substantially prevent fluid flow through the internal flow path, wherein the trigger is biased into the first position; and
 wherein the internal flow path is configured to be connected to an external source of suction; and
 further comprising a lock slidably disposed upon the handle for selective engagement with the trigger to maintain the trigger in the second position wherein the handle further comprises a valve seat operatively connected with the trigger that translates within a flow path housing to block the internal flow path when the trigger is in the second position, and further comprising a first pin extending from the valve seat substantially along the direction of movement of the valve seat and a second pin fixably mounted to the first pin and aligned substantially perpendicularly to the first pin.

10. The apparatus of claim 9, further comprising an aperture on the handle that is fluidly connected to the sheath and the internal flow path, wherein the aperture is configured to allow a tool to pass therethrough and into the internal flow path but substantially prevent fluid flow out of the internal flow path through the aperture.

11. The apparatus of claim 10, wherein the aperture is disposed substantially collinearly with the sheath extending from the handle.

12. The apparatus of claim 9, wherein the second pin is received within an aperture in the trigger to cause the second pin to translate with motion of the trigger.

13. A method for removing fluid and particulate matter within a patient, comprising the steps of:
 providing the apparatus of claim 9,
 inserting the sheath within a patient such that the distal end portion of the sheath is proximate a volume of fluid or particulate matter intended for removal;
 operating the handle constrained with and in fluid communication with the sheath through the internal flow path defined within the handle; and
 connecting an external source of suction to the internal flow path within the handle to allow suction flow through the internal flow path and the first lumen defined within the sheath; and
 controlling the flow of suction through the internal flow path with the trigger disposed upon the handle.

14. The method of claim 13, further step of inserting a device through an aperture in the handle that communicates with and through a second lumen defined in the sheath for operation proximate the volume of fluid or particulate matter intended for removal.

15. A medical device comprising:
 a sheath comprising an extended distal end portion, a proximal end portion, and parallel and segregated first and second lumens defined therethrough, wherein the first and second lumens are defined by first and second tubular members with the second tubular member disposed within the first lumen such that an outer surface of the second tubular member contacts an inner surface of the first tubular member along a length of the sheath;
 a handle fixedly connected to the proximal end portion of the sheath, the handle comprising an operator comprising a trigger pivotably mounted upon the handle that is translatable between a first position and a second position, wherein the trigger biased into the first position;
 a flow path defined within the handle in fluid communication with the proximal end portion of the first lumen of the sheath, wherein the operator is configured to substantially block the flow path when the trigger is in the second position and allow flow therethrough when the trigger is in the first position, wherein the flow path comprises a first inlet portion that is configured to communicate with a remote source of suction; and
 a second inlet portion configured to receive a tool therethrough and allow the tool to extend through the second lumen of the sheath wherein the operator comprises a valve seat that translates with motion of the trigger between the first and second potions, wherein the valve seat rests upon a first pin oriented substantially in the direction of travel of the valve seat, and further comprising a second pin connected with the first pin, the second pin being fixably mounted to the first pin.

16. The medical device of claim 15, wherein the first and second tubular members are stainless steel.

17. The medical device of claim 15, wherein a diameter of the second lumen is significantly smaller than a diameter of the first lumen.

18. The medical device of claim 15, wherein a diameter of the first lumen is one of about 9.5 Fr, 10 Fr, 12 Fr, or 14 Fr and a diameter of the second lumen is about 3 Fr.

\* \* \* \* \*

UNITED STATES PATENT AND TRADEMARK OFFICE
CERTIFICATE OF CORRECTION

PATENT NO. : 7,811,256 B2  
APPLICATION NO. : 12/338590  
DATED : October 12, 2010  
INVENTOR(S) : Jaime Landman et al.

Page 1 of 1

It is certified that error appears in the above-identified patent and that said Letters Patent is hereby corrected as shown below:

On the Title Page

In the left column, Item (73), after "Vance Products Inc." insert --d/b/a Cook Urological Incorporated--.

Signed and Sealed this  
Twenty-eighth Day of December, 2010

David J. Kappos  
*Director of the United States Patent and Trademark Office*